(12) United States Patent
Uesaka et al.

(10) Patent No.: US 9,060,697 B2
(45) Date of Patent: Jun. 23, 2015

(54) BLOOD PRESSURE METER CUFF

(71) Applicant: OMRON HEALTHCARE Co., Ltd., Kyoto (JP)

(72) Inventors: Chisato Uesaka, Kyoto (JP); Takanori Nishioka, Kyoto (JP); Ryosuke Doi, Kyoto (JP); Shingo Yamashita, Kyoto (JP); Yukiya Sawanoi, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 14/391,279

(22) PCT Filed: Apr. 3, 2013

(86) PCT No.: PCT/JP2013/060229
§ 371 (c)(1),
(2) Date: Oct. 8, 2014

(87) PCT Pub. No.: WO2013/157393
PCT Pub. Date: Oct. 24, 2013

(65) Prior Publication Data
US 2015/0105676 A1    Apr. 16, 2015

(30) Foreign Application Priority Data

Apr. 16, 2012    (JP) ................................. 2012-092858

(51) Int. Cl.
*A61B 5/02* (2006.01)
*A61B 5/022* (2006.01)
*A61B 5/00* (2006.01)

(52) U.S. Cl.
CPC ............. *A61B 5/02233* (2013.01); *A61B 5/022* (2013.01); *A61B 5/742* (2013.01); *A61B 5/7475* (2013.01)

(58) Field of Classification Search
CPC .... A61B 5/021; A61B 5/02141; A61B 5/022; A61B 5/02233; A61B 17/132; A61B 17/135
See application file for complete search history.

(56) References Cited

U.S. PATENT DOCUMENTS

| 6,245,023 B1 * | 6/2001 | Clemmons ..................... 600/499 |
| 2002/0099299 A1 * | 7/2002 | Inagaki .......................... 600/499 |
| 2004/0010198 A1 * | 1/2004 | Yamakoshi et al. .......... 600/499 |

(Continued)

FOREIGN PATENT DOCUMENTS

JP    10-57323 A    3/1998

OTHER PUBLICATIONS

International Search Report issued in PCT/JP2013/060229 mailed on May 7, 2013 (2 pages).

(Continued)

*Primary Examiner* — Michael D'Angelo
(74) *Attorney, Agent, or Firm* — Osha Liang LLP

(57) ABSTRACT

A blood pressure meter cuff includes an air bladder that receives a supply of air in order to compress a radial artery and an ulnar artery, and a cuff band for fixing the air bladder to a wrist including the radial artery and the ulnar artery. The air bladder has a wide portion that is arranged on the radial artery and the ulnar artery, and first and second narrow portions that are continuous with the wide portion and are narrower than the wide portion. The edges of the first and second narrow portions that are continuous with the edges of the wide portion are shaped as straight lines that are inclined with respect to the width direction.

15 Claims, 5 Drawing Sheets

(56) References Cited

U.S. PATENT DOCUMENTS

| | | |
|---|---|---|
| 2005/0171445 A1* | 8/2005 | Millay et al. .................. 600/499 |
| 2006/0058688 A1* | 3/2006 | Kishimoto et al. ........... 600/499 |
| 2006/0129049 A1* | 6/2006 | Sano et al. .................... 600/499 |
| 2006/0135876 A1* | 6/2006 | Andresen et al. ............. 600/513 |
| 2014/0276147 A1* | 9/2014 | Gloth et al. ................... 600/499 |

OTHER PUBLICATIONS

Written Opinion of the International Searching Authority issued in PCT/JP2013/060229 mailed on May 7, 2013 (8 pages).

* cited by examiner

BLOOD PRESSURE METER CUFF

TECHNICAL FIELD

The present invention relates to a blood pressure meter cuff used in an upper-arm blood pressure meter, a wrist blood pressure meter, or the like, for example.

BACKGROUND ART

As disclosed in JP 10-57323A (Patent Literature 1), there are conventional blood pressure meter cuffs that include a cuff band configured to be wrapped around a wrist, and an air bladder that is provided in the cuff band and receives a supply of air in order to compress an artery of the wrist.

With the conventional blood pressure meter cuff, a reduction in the capacity of the air bladder is achieved due to the air bladder having a cross shape in a plan view. More specifically, the air bladder is composed of a wide portion with a large width (length in a direction orthogonal to the direction of wrapping around the wrist), and narrow portions that are provided on the two sides in the wrapping direction of the large-width portion and are narrower than the wide portion.

CITATION LIST

Patent Literature

Patent Literature 1: JP 10-57323A

SUMMARY OF INVENTION

Technical Problem

With the conventional blood pressure meter cuff, the air bladder is cross-shaped in a plan view, and therefore a portion extending in the width direction in the air bladder and a portion extending in the wrapping direction in the air bladder intersect each other at a right angle. In other words, the wide portion and the narrow portion form a right angle.

As a result, when air is supplied to the air bladder, stress is concentrated at the boundary between the wide portion and the narrow portion, and therefore there is a problem in that tearing is likely to occur at the right angle portion.

In view of this, it is an object of the present invention to provide a blood pressure meter cuff that can reduce the capacity of a fluid bladder and make tearing less likely to occur when a fluid is supplied to the fluid bladder.

Solution to Problem

In order to solve the above-described problem, a blood pressure meter cuff according to the present invention includes:

a fluid bladder that receives a supply of fluid in order to compress an artery; and a fixing means for fixing the fluid bladder to a measurement area that includes the artery, wherein the fluid bladder includes:

a wide portion arranged on the artery, and a narrow portion that is continuous with the wide portion and is narrower than the wide portion, and the edge of the narrow portion that is continuous with the edge of the wide portion is shaped as an approximately straight line that is inclined with respect to the width direction.

Here, examples of approximately straight lines include a straight line and a shape obtained by forming a portion of a straight line (e.g., an end thereof) into a curved line.

According to the above configuration, since the fluid bladder has a narrow portion that is narrower than the wide portion, the capacity of the fluid bladder can be reduced.

Also, the edge of the narrow portion that is continuous with the edge of the wide portion is shaped as an approximately straight line that is inclined with respect to the width direction, and therefore, the wide portion and the narrow portion can be made to form an obtuse angle. Accordingly, when a fluid is supplied to the fluid bladder, stress is not concentrated at the boundary between the wide portion and the narrow portion, and it is possible to make tearing less likely to occur.

With the blood pressure meter cuff according to an embodiment, the narrow portion is provided at one end in a direction orthogonal to the width direction of the fluid bladder.

According to the embodiment, by providing the narrow portion at one end in a direction orthogonal to the width direction of the fluid bladder, the artery can be sufficiently compressed even if the capacity of the fluid bladder is reduced.

With the blood pressure meter cuff according to an embodiment, the narrow portion is provided at the central portion in a direction orthogonal to the width direction of the fluid bladder.

According to the embodiment, by providing the narrow portion at the central portion in a direction orthogonal to the width direction of the fluid bladder, the capacity of the fluid bladder can be further reduced.

With the blood pressure meter cuff according to an embodiment, a partition portion that partitions the interior of the fluid bladder into a plurality of spaces is provided in the fluid bladder.

According to the embodiment, since there is a partition portion that partitions the interior of the fluid bladder into a plurality of spaces, it is possible to reduce the capacity of the fluid bladder by the capacity corresponding to the partition portion.

With the blood pressure meter cuff according to an embodiment, the partition portion is provided at the center in a direction orthogonal to the width direction of the fluid bladder.

According to the above embodiment, in the case where the fluid bladder is fixed to the wrist by the fixing means, the partition portion is provided in the center in the direction orthogonal to the width direction of the fluid bladder, and it is thereby possible for one of the spaces in the fluid bladder to be located on the ulnar artery and the other of the spaces in the fluid bladder to be located on the radial artery. Accordingly, the ulnar artery and the radial artery can be reliably compressed.

With the blood pressure meter cuff according to an embodiment, the partition portion is provided so as to be off-center toward one end in a direction orthogonal to the width direction of the fluid bladder.

According to the above embodiment, if the fluid bladder is fixed to the wrist using the fixing means, the partition portion is provided so as to be off-center toward one end in a direction orthogonal to the width direction of the fluid bladder, and thereby one of the spaces in the fluid bladder can be made larger than the other space in the fluid bladder. Accordingly, if the largest of the spaces in the fluid bladder is located on the ulnar artery, it is possible to compress the ulnar artery, which is located deeper than the radial artery.

With the blood pressure meter cuff according to an embodiment, the length in the direction orthogonal to the width direction of the wide portion is ½ to ¾ the length in the direction orthogonal to the width direction of the fluid bladder.

According to the above embodiment, if the fluid bladder is fixed to the wrist using the fixing means, the length in the direction orthogonal to the width direction of the wide portion is ½ to ¾ the length in the direction orthogonal to the width direction of the fluid bladder, and therefore it is possible to avoid compressing only one of the ulnar artery and the radial artery.

Advantageous Effects of the Invention

The blood pressure meter cuff according to the present invention includes a fluid bladder that receives a supply of fluid in order to compress an artery, and the fluid bladder has a wide portion arranged on the artery and a narrow portion that is continuous with the wide portion and is narrower than the wide portion, and therefore the capacity of the fluid bladder can be reduced.

Also, the edge of the narrow portion that is continuous with the edge of the wide portion is shaped as an approximately straight line that is inclined with respect to the width direction, and therefore the wide portion and the narrow portion can be made to form an obtuse angle and stress can be prevented from being concentrated at the boundary between the wide portion and the narrow portion. Accordingly, it is possible to make tearing less likely to occur when a fluid is supplied to the fluid bladder.

DESCRIPTION OF EMBODIMENTS

Figure 1:
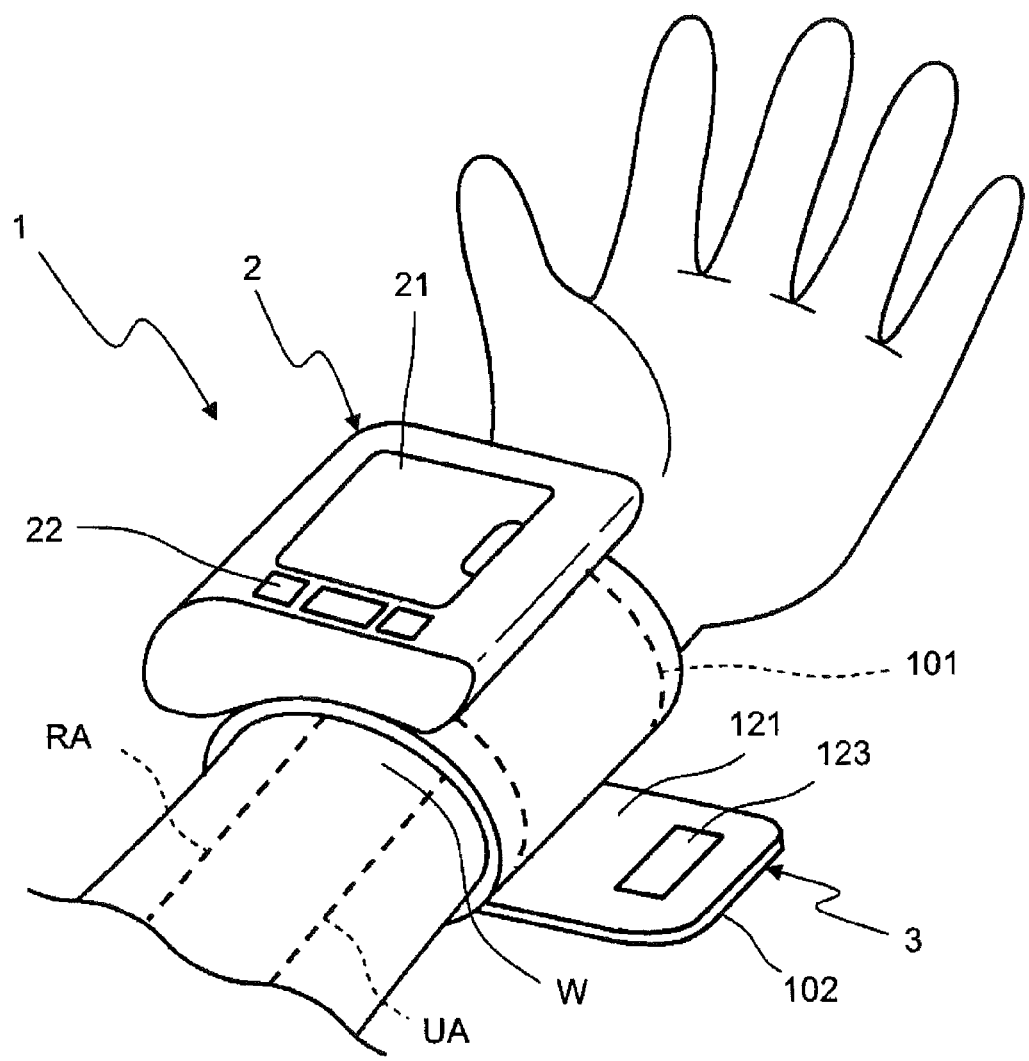
FIG. 1 is a schematic perspective view of an attached state of a wrist blood pressure meter according to an embodiment of the present invention.

Hereinafter, a blood pressure meter cuff 3 of the present invention will be described in detail according to the embodiments shown in the drawings.

FIG. 1 is a schematic perspective view of a state in which a wrist blood pressure meter 1 of an embodiment of the present invention has been attached to a wrist W, as viewed from obliquely above.

The blood pressure meter 1 includes a blood pressure meter main body 2, and a blood pressure meter cuff 3 having a circumferential face to which the blood pressure meter main body 2 is attached, by which blood pressure is measured by compressing a radial artery RA and an ulnar artery UA in the wrist W. Note that the wrist W is an example of a measurement area.

A display unit 21 that displays various types of information, including a blood pressure value, and an operation unit 22 that is operated in order to input various types of instructions for measurement are provided on the surface of the blood pressure meter main body 2. Also, a pump that supplies air to an air bladder 101 in the blood pressure meter cuff 3, a pressure sensor that changes an output value according to the internal pressure of the air bladder 101 (referred to below as "cuff pressure"), and a control apparatus that controls the pump, the pressure sensor, and the like are built into the blood pressure meter main body 2, although these are not shown in the drawing.

Figure 2:
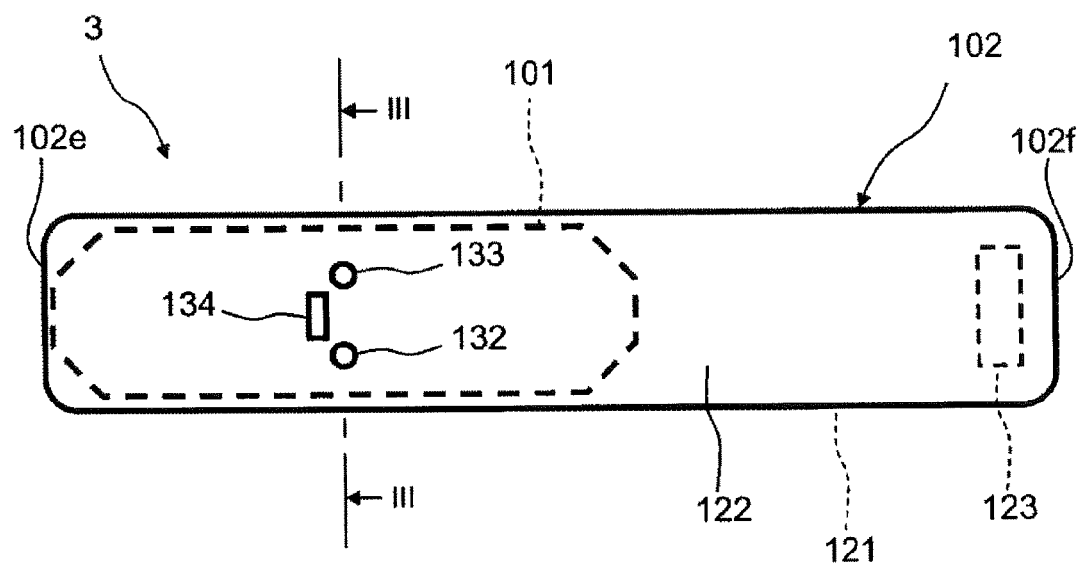
FIG. 2 is a schematic plan view of a blood pressure meter cuff according to an embodiment of the present invention.

FIG. 2 is a schematic plan view of the blood pressure meter cuff 3 as viewed from the blood pressure meter main body 2 side. Also, FIG. 3 is a schematic cross-sectional view taken along line III-III in FIG. 2.

Figure 3:
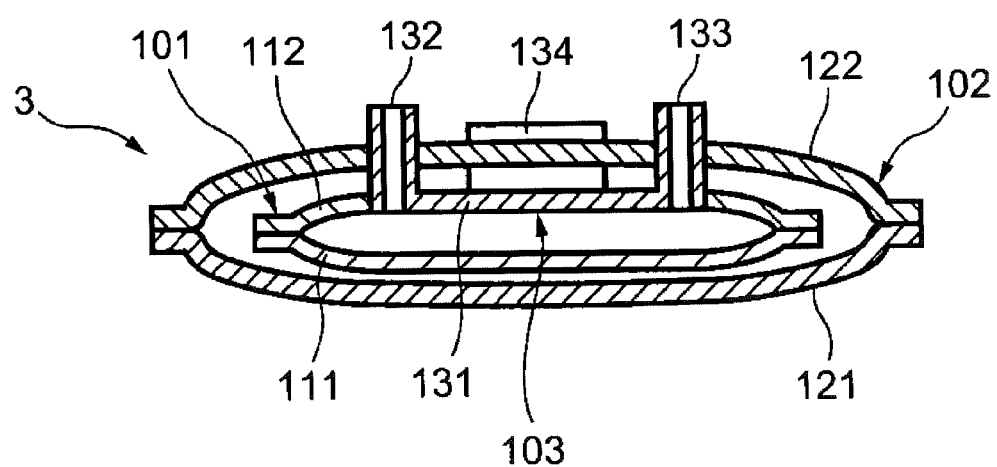
FIG. 3 is a schematic cross-sectional view taken along line in FIG. 2.

As shown in FIGS. 2 and 3, the blood pressure meter cuff 3 includes the air bladder 101 that has an octagonal shape in a plan view, a cuff band 102 for fixing the air bladder 101 to the wrist W, and a connecting member 103 that connects the air bladder 101 to the cuff band 102. Note that the air bladder 101 is an example of a fluid bladder, and the cuff band 102 is an example of a fixing means. In FIG. 2, the longitudinal direction corresponds to the width direction of the cuff band 102 and the air bladder 101, and the lateral direction corresponds to the length direction of the cuff band 102 and the air bladder 101 (the direction orthogonal to the width direction). The two ends in the length direction of the cuff band 102 are indicated by reference numerals 102e and 102f.

The air bladder 101 is arranged in the space within the cuff band 102 such that it is closer to the end portion 102e side in the length direction of the cuff band 102. The air bladder 101 has an inner sheet 111 arranged on the wrist W side, and an outer sheet 112 arranged on the blood pressure meter main body 2 side. Also, when air is supplied to the air bladder 101 from the pump, the air bladder 101 expands and compresses the radial artery RA and the ulnar artery UA. This type of air bladder 101 is obtained by preparing the inner sheet 111 and the outer sheet 112, which are approximately the same shape, and welding the circumferential edge portion of the inner sheet 111 and the circumferential edge portion of the outer sheet 112 together. The material of the inner sheet 111 and the outer sheet 112 may be anything, as long as it is high in elasticity and air does not leak from the circumferential edge portion after being welded. Specifically, EVA (ethylene-vinyl acetate copolymer), PVC (flexible polyvinyl chloride), PU (polyurethane), TPE-O (olefin-based thermoplastic elastomer), natural rubber, and the like are examples of materials for the inner sheet 111 and the outer sheet 112.

The cuff band 102 has an inner cloth 121 opposing the inner sheet 111, and an outer cloth 122 opposing the outer sheet 112. When the cuff band 102 is wrapped around the wrist W, most of the inner cloth 121 is in direct contact with the wrist W. Also, the shape of the outer cloth 122 and the inner cloth 121 in a plan view is approximately rectangular, and the circumferential edge portion of the outer cloth 122 and the circumferential edge portion of the inner cloth 121 are sewn together. Also, a polyester surface fastener 123 is provided on the external face of the end portion 102f (on the surface of the side opposite to the air bladder 101 side) in the length direction of the inner cloth 121 (in the direction in which the cuff band 102 is wrapped around the wrist W). Also, polyester fiber or the like is used as the material of the outer cloth 122, and polyamide or polyurethane fiber or the like is used as the material of the inner cloth 121, for example.

The connecting member 103 has a base portion 131 that is formed by welding the circumferential edge thereof to the outer sheet 112, a first tube portion 132 for letting air in and out of the air bladder, a second tube portion 133 for detecting the cuff pressure, and a hook portion 134 whose distal end portion engages with the outer cloth 122. The base portion 131, the first tube portion 132, the second tube portion 133, and the hook portion 134 are integrally formed by resin molding. Also, the first tube portion 132 and the second tube portion 133 extend from the base portion 131 to the outer cloth 122 side, and the distal end portions thereof protrude from the outer cloth 122. Also, similarly to the first tube portion 132 and the second tube portion 133, the hook portion 134 also extends from the base portion 131 to the outer cloth 122 side and the distal end portion thereof protrudes from the outer cloth 122, and the distal end portion is bent in a reversed L shape in a side view (see FIG. 5).

Figure 4:
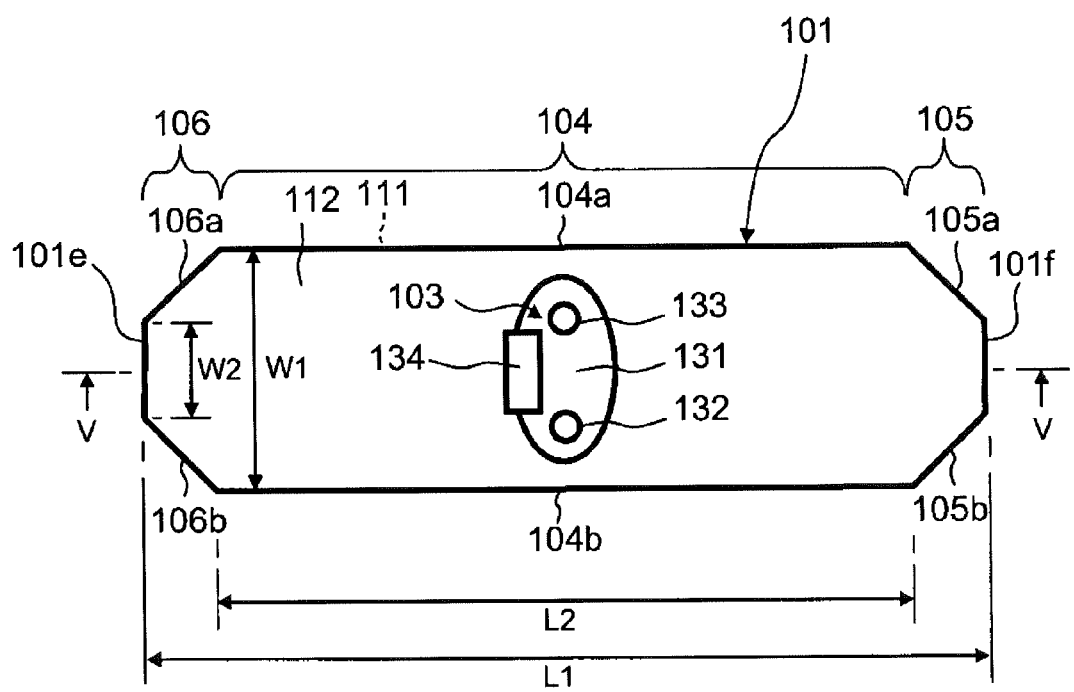
FIG. 4 is a schematic plan view of an air bladder according to an embodiment of the present invention.

FIG. 4 is a schematic plan view of the air bladder 101 as viewed from the blood pressure meter main body 2 side. Also, FIG. 5 is a schematic cross-sectional view as viewed from line V-V in FIG. 4.

Figure 5:
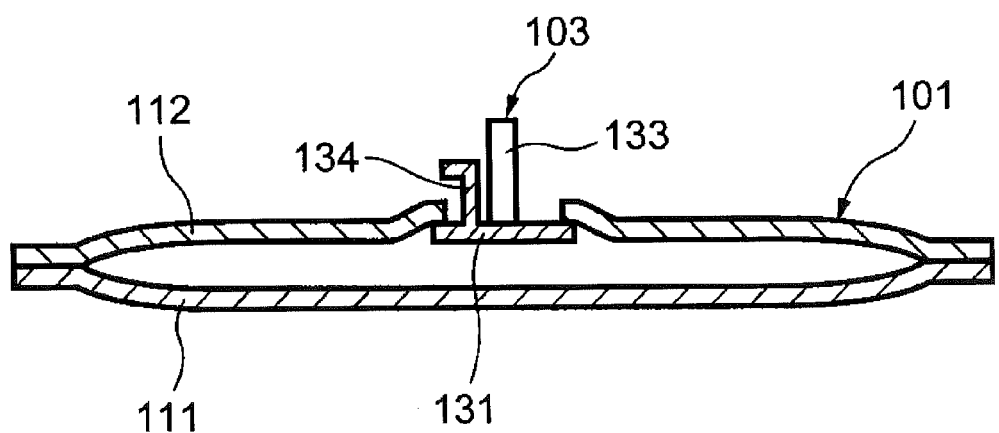
FIG. 5 is a schematic cross-sectional view taken along line V-V in FIG. 4.

As shown in FIGS. 4 and 5, the air bladder 101 has a wide portion 104 that is arranged on the radial artery RA and the ulnar artery UA, a first narrow portion 105 that is continuous with one end in the length direction of the wide portion 104 (the direction in which the cuff band 102 is wrapped around the wrist W) and is narrower than the wide portion 104, and a second narrow portion 106 that is continuous with the other end in the length direction of the wide portion 104 (the direction in which the cuff band 102 is wrapped around the wrist W) and is narrower than the wide portion 104. A length L1 in the length direction of the air bladder 101 is set to 140 mm for example. Note that the first narrow portion 105 and the second narrow portion 106 are examples of narrow portions provided at respective ends in the length direction.

The shape of the wide portion 104 is rectangular in a plan view. A length L2 in the length direction of the wide portion 104 is set to 100 mm for example.

Let the two end portions in the length direction of the air bladder 101 be denoted by the reference numerals 101e and 101f. The first narrow portion 105 is provided on the end portion 101f in the length direction of the air bladder 101, whereas the second narrow portion 106 is provided on the end portion 101e in the length direction of the air bladder 101. The first and second narrow portions 105 and 106 each have a shape that gradually becomes narrow the farther it is from the wide portion 104. More specifically, the width W1 of the wide portion 104 side of the first narrow portion 105 and the second narrow portion 106 is set to 60 mm, for example, and the width W2 of the side opposite to the wide portion 104 side of the first narrow portion 105 and the second narrow portion 106 is set to 20 mm, for example. Also, the edges 105a and 106a of the first and second narrow portions 105 and 106 that are continuous with the edge 104a of the wide portion 104 are shaped as straight lines that are inclined with respect to the width direction. Also, the edges 105b and 106b of the first and second narrow portions 105 and 106 that are continuous with the edge 104b of the wide portion 104 are also shaped as straight lines that are inclined with respect to the width direction. That is to say, the shapes of the first and second narrow portions 105 and 106 in a plan view are trapezoids that have been rotated 90°.

With the blood pressure meter cuff 3 having the above configuration, the air bladder 101 has the first and second narrow portions 105 and 106 that are narrower than the wide portion 104, and therefore the capacity of the air bladder 101 can be reduced. Accordingly, it is possible to realize a reduction in the size of the pump and a reduction in the size and thickness of the blood pressure meter 1.

Also, the edges 105a, 105b, 106a, and 106b of the first and second narrow portions 105 and 106 that are continuous with the edges 104a and 104b of the wide portion 104 are shaped as straight lines that are inclined with respect to the width direction. Accordingly, the edge 104a of the wide portion 104 and the edges 105a and 106a of the first and second narrow portions 105 and 106 form obtuse angles, and the edge 104b of the wide portion 104 and the edges 105b and 106b of the first and second narrow portions 105 and 106 form obtuse angles. Accordingly, when air is supplied to the air bladder 101, it is possible to prevent stress from being concentrated at the boundary between the wide portion 104 and the first and second narrow portions 105 and 106, and to prevent the air bladder 101 from tearing easily.

Also, since the first narrow portion 105 is provided at one end portion in the length direction of the air bladder 101 and the second narrow portion 106 is provided at the other end portion in the length direction of the air bladder 101, the wide portion 104 is reliably arranged on the radial artery RA and the ulnar artery UA, and the radial artery RA and the ulnar artery UA can be sufficiently compressed. Accordingly, even if the air bladder 101 has the first and second narrow portions 105 and 106, good accuracy in the blood pressure measurement can be achieved.

In the above embodiment, an air bladder 101 that receives a supply of air in order to compress an artery was used, but a fluid bladder that receives a supply of a fluid in order to compress an artery may be used.

In the above embodiment, the edges 105a, 105b, 106a, and 106b of the first and second narrow portions 105 and 106 that are continuous with the edges 104a and 104b of the wide portion 104 are shaped as straight lines that are inclined with respect to the width direction, but it is possible for them to have shapes obtained by forming a portion of a straight line (e.g., the end portion) into a curved line.

In the above embodiment, an example was described in which the blood pressure meter cuff of the present invention was applied to a wrist blood pressure meter, but the blood pressure meter to which the blood pressure meter cuff of the present invention is applied is not limited to a wrist blood pressure meter. In other words, the blood pressure meter to which the blood pressure meter cuff of the present invention is applied may be a blood pressure meter that is attached at any location on the human body, such as an upper arm, a thigh, an ankle, a finger, or the like.

In the above embodiment, the air bladder 101 was covered by a cuff band and was not in contact with the measurement area, but it may be in contact with the measurement area.

In the above embodiment, it is preferable that the length L2 in the length direction of the wide portion 104 is ½ to ¾ the length L1 in the length direction of the air bladder 101. That is to say, it is preferable that the length L2 is set to be within a range from ½ L1 to ¾ L1. If set in this manner, it is possible to avoid a situation in which only one of the ulnar artery UA and the radial artery RA can be compressed.

Figure 6:
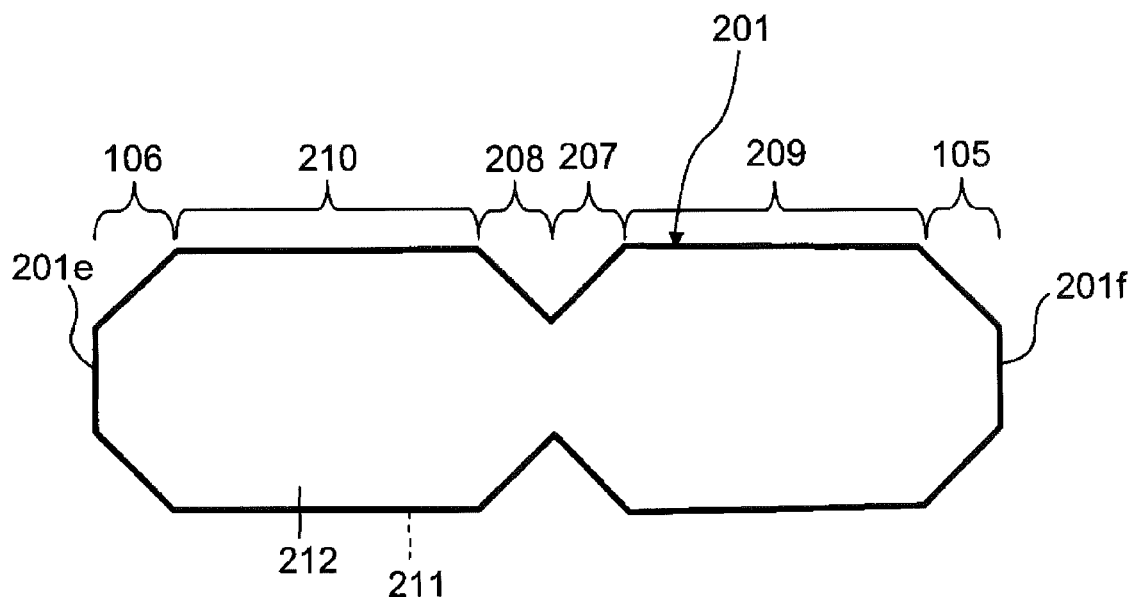
FIG. 6 is a schematic plan view of an air bladder according to another embodiment of the present invention.

In the above embodiment, the blood pressure meter cuff included the air bladder 101 shown in FIG. 4, but it may include an air bladder 201 shown in FIG. 6.

Let the two ends in the length direction of the air bladder 201 be denoted by the reference numerals 201e and 201f. Similarly to the air bladder 101, the air bladder 201 has a first narrow portion 105 on the end portion 201f in the length direction and has a second narrow portion 106 on the end portion 201e in the length direction. Also, third and fourth narrow portions 207 and 208 are provided at the central portion in the length direction of the air bladder 201. Also, the first wide portion is provided between the first narrow portion 105 and the third narrow portion 207, and a second wide portion is provided between the second narrow portion 106 and the fourth narrow portion 208. The first and second wide portions 209 and 210 are wider than the first narrow portion 105, the second narrow portion 106, the third narrow portion 207, and the fourth narrow portion 208. More specifically, the first narrow portion 105 is continuous with one end in the length direction of the first wide portion 209 and gradually becomes narrower the farther it is from the first wide portion 209. Also, the second narrow portion 106 is continuous with the other end in the length direction of the second wide portion 210 and gradually becomes narrower the farther it is from the second wide portion 210. Also, the third narrow portion 207 is continuous with the other end in the length direction of the first wide portion 209 and gradually becomes narrower the farther it is from the first wide portion 209. Also, the fourth narrow portion 208 is continuous with one end in the length direction of the second wide portion 210 and gradually becomes narrower the farther it is from the second wide portion 210. Note that the third and fourth narrow portions 207 and 208 are examples of narrow portions that are provided in the central portion in the length direction.

Also, the air bladder 201 is obtained by preparing an inner sheet 211 and an outer sheet 212 that are approximately the same shape and welding the circumferential edge of the inner sheet 211 and the circumferential edge of the outer sheet 212 together. The materials of the inner sheet 211 and the outer sheet 212 are the same as the materials of the inner sheet 111 and the outer sheet 112.

The capacity is reduced to a greater extent with this type of air bladder 201 than with the air bladder 101. Moreover, the first wide portion 209 is arranged on the ulnar artery UA and the second wide portion 210 is arranged on the radial artery RA, and it is thereby possible to sufficiently compress the radial artery RA and the ulnar artery UA.

Figure 7:
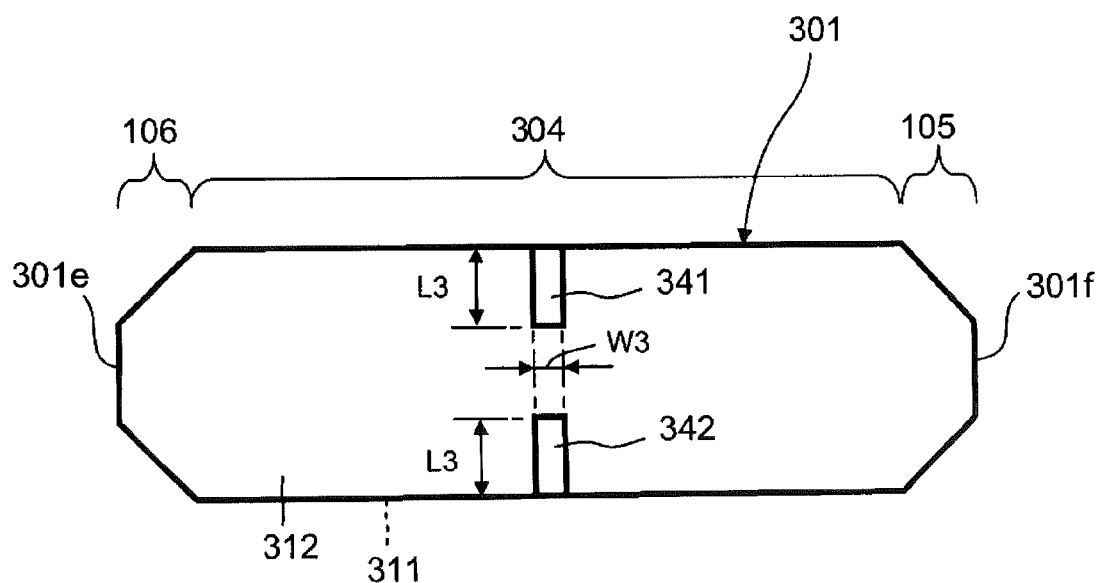
FIG. 7 is a schematic plan view of an air bladder according to another embodiment of the present invention.

In the above embodiment, the blood pressure meter cuff included the air bladder 101 shown in FIG. 4, but it may include an air bladder 301 shown in FIG. 7.

Let the two ends in the length direction of the air bladder 301 be denoted by the reference numerals 301e and 301f. Similarly to the air bladder 101, the air bladder 301 has a first narrow portion 105 on the end portion 301f in the length direction and has a second narrow portion 106 on the end portion 301e in the length direction. Also, the air bladder 301 has a wide portion 304 between the first narrow portion 105 and the second narrow portion 106. The wide portion 304 is wider than the first and second narrow portions 105 and 106. Also, first and second welded portions 341 and 342 that partition the interior of the air bladder 301 into multiple spaces are provided in the wide portion 304. The first and second welded portions 341 and 342 are positioned in the center in the length direction of the air bladder 301, and a pre-set gap is formed between the first welded portion 341 and the second welded portion 342. Also, the space on the first narrow portion 105 side in the air bladder 301, and the space on the second narrow portion 106 side in the air bladder 301 are in communication via the space between the first welded portion 341 and the second welded portion 342. Also, at the first and second welded portions 341 and 342, a length L3 is set to 10 mm, for example, and a width W3 is set to 5 mm, for example. Note that the first and second welded portions 341 and 342 are examples of partition portions.

Also, the air bladder 301 is obtained by preparing an inner sheet 311 and an outer sheet 312 that are approximately the same shape, welding the circumferential edge of the inner sheet 311 and the circumferential edge of the outer sheet 312 together, and welding a portion of the central portion in the length direction of the inner sheet 311 and a portion of the central portion in the length direction of the outer sheet 312 together. The materials of the inner sheet 311 and the outer sheet 312 are the same as the materials of the inner sheet 111 and the outer sheet 112.

The capacity is reduced to a greater extent with this type of air bladder 301 than with the air bladder 101. Moreover, a portion on the first narrow portion 105 side with respect to the first and second welded portions 341 and 342 of the wide portion 304 is arranged on the ulnar artery UA, and a portion on the second narrow portion 106 side with respect to the first and second welded portions 341 and 342 of the wide portion 304 is arranged on the radial artery RA, and it is thereby possible to sufficiently compress the radial artery RA and the ulnar artery UA.

Also, for example, a block-shaped member or a plate-shaped member may be used as an example of a partition portion instead of the first and second welded portions 341 and 342. The block-shaped member and the plate-shaped member may be arranged in the air bladder 301 and be in contact with the inner sheet 311 and the outer sheet 312.

Figure 8:
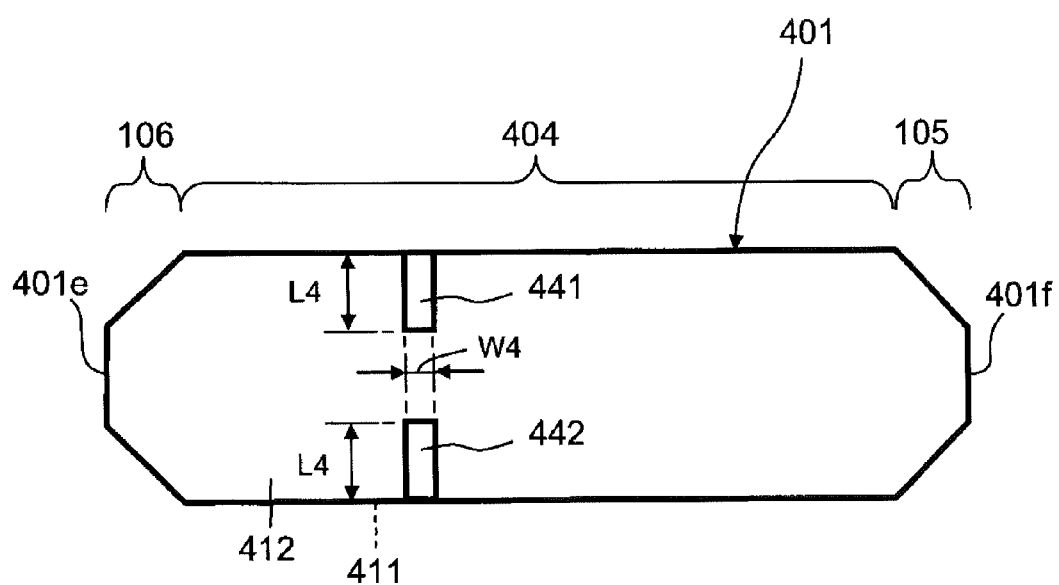
FIG. 8 is a schematic plan view of an air bladder according to another embodiment of the present invention.

In the above embodiment, the blood pressure meter cuff included the air bladder 101 shown in FIG. 4, but it may include an air bladder 401 shown in FIG. 8.

Let the two ends in the length direction of the air bladder 401 be denoted by the reference numerals 401e and 401f. Similarly to the air bladder 101, the air bladder 401 has a first narrow portion 105 on the end portion 401f in the length direction and has a second narrow portion 106 on the end portion 401e in the length direction. Also, the air bladder 401 has a wide portion 404 between the first narrow portion 105 and the second narrow portion 106. The wide portion 404 is wider than the first and second narrow portions 105 and 106. Also, first and second welded portions 441 and 442 that partition the interior of the air bladder 401 into multiple spaces are provided in the wide portion 404. The first and second welded portions 441 and 442 are off-center toward the second narrow portion 106 in the length direction of the air bladder 401, and the first and second welded portions 441 and 442 may be aligned in the width direction with a pre-set gap therebetween. Also, the space on the first narrow portion 105 side in the air bladder 401, and the space on the second narrow portion 106 side in the air bladder 401 are in communication via the space between the first welded portion 441 and the second welded portion 442. Also, at the first and second welded portions 441 and 442, a length L4 is set to 10 mm, for example, and a width W4 is set to 5 mm, for example. Note that the first and second welded portions 441 and 442 are examples of partition portions.

Also, the air bladder 401 is obtained by preparing an inner sheet 411 and an outer sheet 412 that are approximately the same shape, welding the circumferential edge of the inner sheet 411 and the circumferential edge of the outer sheet 412 together, and welding the portion that is off-center toward an end portion in the length direction of the inner sheet 411 and the portion that is off-center toward an end portion in the length direction of the outer sheet 412 together. The materials of the inner sheet 411 and the outer sheet 412 are the same as the materials of the inner sheet 111 and the outer sheet 112.

The capacity is reduced to a greater extent with this type of air bladder 401 than with the air bladder 101. Moreover, a portion on the first narrow portion 105 side with respect to the first and second welded portions 441 and 442 of the wide portion 404 is arranged on the ulnar artery UA, and a portion on the second narrow portion 106 side with respect to the first and second welded portions 441 and 442 of the wide portion 404 is arranged on the radial artery RA, and it is thereby possible to sufficiently compress the radial artery RA and the ulnar artery UA.

Also, the portion on the second narrow portion 106 side with respect to the first and second welded portions of the wide portion 404 has a larger capacity than the portion on the first narrow portion 105 side with respect to the first and second welded portions of the wide portion 404, and therefore it is possible to appropriately compress the ulnar artery UA, which is located deeper than the radial artery RA.

Also, for example, a block-shaped member or a plate-shaped member may be used as an example of a partition portion instead of the first and second welded portions 441 and 442. The block-shaped member and the plate-shaped member may be arranged in the air bladder 401 and be in contact with the inner sheet 411 and the outer sheet 412.

Note that in FIGS. 6 to 8, constituent elements that are the same as the constituent elements in FIG. 4 are denoted by reference numerals that are the same as those of the constituent elements in FIG. 4.

Also, a connecting member that is similar to the connecting member 103 may be attached to the air bladder 201, 301, and 401.

Also, in the embodiment and the variations thereof, a description was given envisioning a case in which the wrist blood pressure meter 1 and the modified examples thereof were attached to the wrist W of a left hand, but effects similar to those described above can be obtained also when the wrist blood pressure meter 1 and the modified examples thereof are attached to the wrist of a right hand.

REFERENCE SIGNS LIST

101, 201, 301, 401 Air bladder
102 Cuff band
103 Connecting member
104, 304, 404 Wide portion
104a, 104b, 105a, 105b, 106a, 106b Edge
105 First narrow portion
106 Second narrow portion
207 Third narrow portion
208 Fourth narrow portion
209 First wide portion
210 Second wide portion
341, 441 First welded portion
342, 442 Second welded portion
RA Radial artery
UA Ulnar artery
W Wrist

The invention claimed is:

1. A blood pressure meter cuff comprising:
   a fluid bladder that receives a supply of fluid in order to compress an artery; and
   a fixing means for fixing the fluid bladder to a measurement area that includes the artery,
   wherein the fluid bladder comprises:
      a wide portion arranged on the artery, and
      a narrow portion that is continuous with the wide portion and is narrower than the wide portion, and
   wherein an edge of the narrow portion that is continuous with the edge of the wide portion is shaped as an approximately straight line that is inclined with respect to a width direction of the wide portion.

2. The blood pressure meter cuff according to claim 1, wherein the narrow portion is provided at one end in a direction orthogonal to the width direction of the fluid bladder.

3. The blood pressure meter cuff according to claim 2, wherein the narrow portion is provided at the central portion in a direction orthogonal to the width direction of the fluid bladder.

4. The blood pressure meter cuff according to claim 2, wherein a partition portion that partitions the interior of the fluid bladder into a plurality of spaces is provided in the fluid bladder.

5. The blood pressure meter cuff according to claim 2, wherein the length in the direction orthogonal to the width direction of the wide portion is ½ to ¾ the length in the direction orthogonal to the width direction of the fluid bladder.

6. The blood pressure meter cuff according to claim 1, wherein the narrow portion is provided at the central portion in a direction orthogonal to the width direction of the fluid bladder.

7. The blood pressure meter cuff according to claim 6, wherein a partition portion that partitions the interior of the fluid bladder into a plurality of spaces is provided in the fluid bladder.

8. The blood pressure meter cuff according to claim 6, wherein the length in the direction orthogonal to the width direction of the wide portion is ½ to ¾ the length in the direction orthogonal to the width direction of the fluid bladder.

9. The blood pressure meter cuff according to claim 1, wherein a partition portion that partitions the interior of the fluid bladder into a plurality of spaces is provided in the fluid bladder.

10. The blood pressure meter cuff according to claim 9, wherein the partition portion is provided at the center in a direction orthogonal to the width direction of the fluid bladder.

11. The blood pressure meter cuff according to claim 10, wherein the length in the direction orthogonal to the width direction of the wide portion is ½ to ¾ the length in the direction orthogonal to the width direction of the fluid bladder.

12. The blood pressure meter cuff according to claim 9, wherein the partition portion is provided so as to be off-center toward one end in a direction orthogonal to the width direction of the fluid bladder.

13. The blood pressure meter cuff according to claim 12, wherein the length in the direction orthogonal to the width direction of the wide portion is ½ to ¾ the length in the direction orthogonal to the width direction of the fluid bladder.

14. The blood pressure meter cuff according to claim 9, wherein the length in the direction orthogonal to the width direction of the wide portion is ½ to ¾ the length in the direction orthogonal to the width direction of the fluid bladder.

15. The blood pressure meter cuff according to claim 1, wherein the length in the direction orthogonal to the width direction of the wide portion is ½ to ¾ the length in the direction orthogonal to the width direction of the fluid bladder.

* * * * *